United States Patent
Drasler et al.

(10) Patent No.: US 10,238,395 B2
(45) Date of Patent: Mar. 26, 2019

(54) ARTERIAL WALL COMPRESSION STENT

(71) Applicants: William Joseph Drasler, Minnetonka, MN (US); William Joseph Drasler, II, Minnetonka, MN (US)

(72) Inventors: William Joseph Drasler, Minnetonka, MN (US); William Joseph Drasler, II, Minnetonka, MN (US)

( * ) Notice: Subject to any disclaimer, the term of this patent is extended or adjusted under 35 U.S.C. 154(b) by 228 days.

(21) Appl. No.: 15/262,992

(22) Filed: Sep. 12, 2016

(65) Prior Publication Data
US 2018/0070954 A1 Mar. 15, 2018

(51) Int. Cl.
*A61F 2/06* (2013.01)
*A61B 17/12* (2006.01)
*A61F 2/92* (2013.01)
*A61F 2/958* (2013.01)

(52) U.S. Cl.
CPC .. *A61B 17/12131* (2013.01); *A61B 17/12031* (2013.01); *A61B 17/12109* (2013.01); *A61F 2/92* (2013.01); *A61B 2017/1205* (2013.01); *A61F 2/958* (2013.01)

(58) Field of Classification Search
CPC .... A61F 2/92; A61F 2/95; A61F 2/954; A61F 2/958; A61F 2/962; A61F 2/06; A61B 17/12131; A61B 17/12118; A61B 17/12109; A61B 17/12031
See application file for complete search history.

(56) References Cited

U.S. PATENT DOCUMENTS

| | | | | |
|---|---|---|---|---|
| 4,273,128 | A * | 6/1981 | Lary | A61B 17/22031 |
| | | | | 604/913 |
| 5,002,560 | A * | 3/1991 | Machold | A61F 2/90 |
| | | | | 604/104 |
| 2013/0138081 | A1 * | 5/2013 | Stankus | A61F 2/958 |
| | | | | 604/509 |
| 2016/0038280 | A1 * | 2/2016 | Morriss | A61F 2/2436 |
| | | | | 623/2.18 |

* cited by examiner

*Primary Examiner* — Victor Nguyen

(57) ABSTRACT

A compression stent for applying a localized high stress against a blood vessel wall to cause vessel wall compression and blockage of sympathetic and nerve signal transmission within the wall of a blood vessel. The compression stent can also sever nerves located in the vessel wall. Blockage of sympathetic nerve signal transmission reduces hypertension and improves other clinical problems that are associated with sympathetic nerve signals.

7 Claims, 22 Drawing Sheets

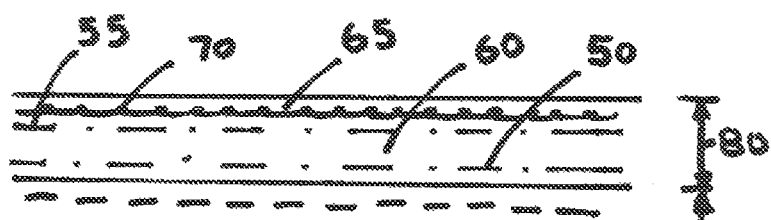
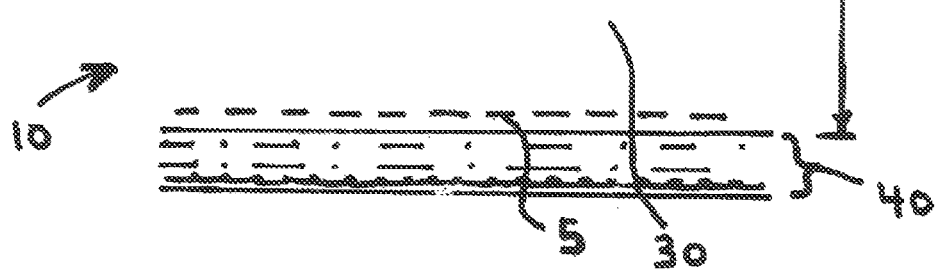
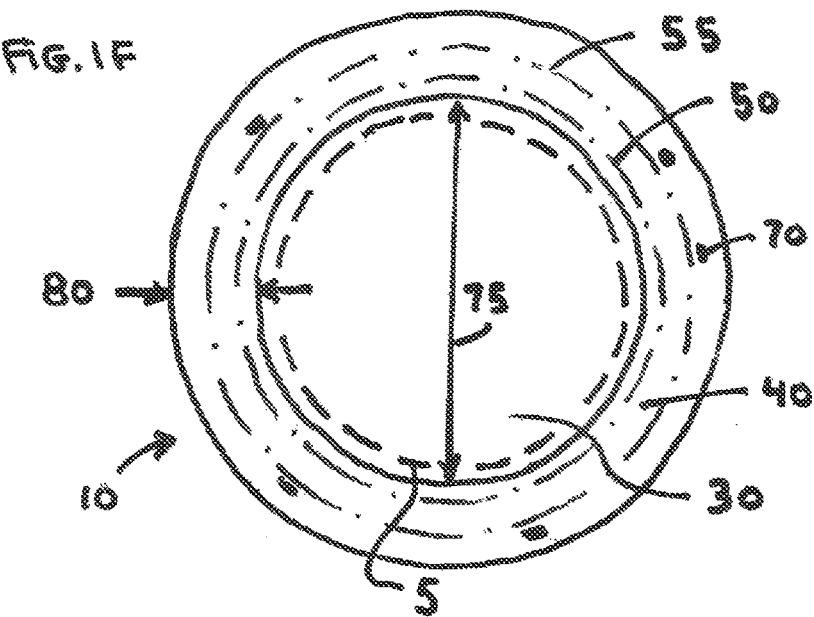

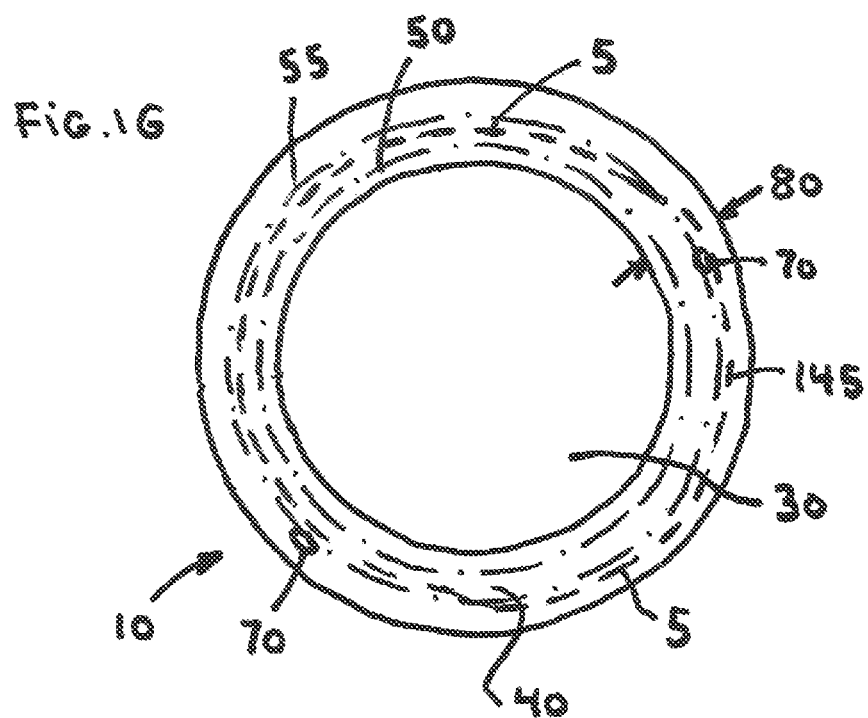

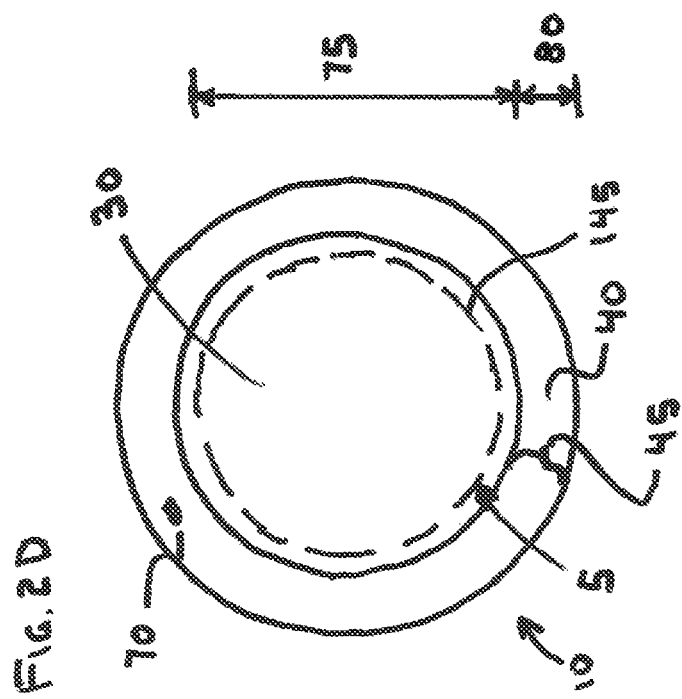
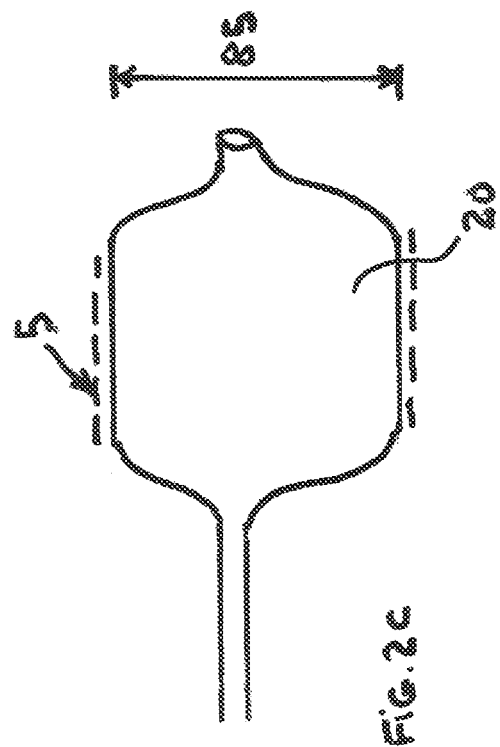

FIG. 3
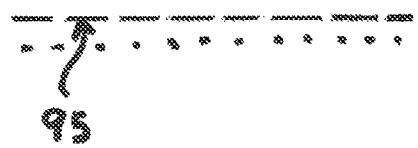
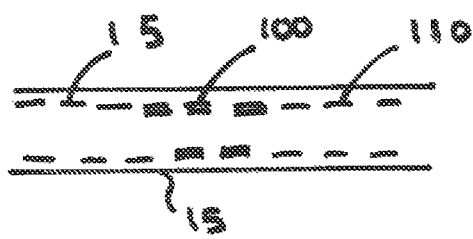
FIG. 4A
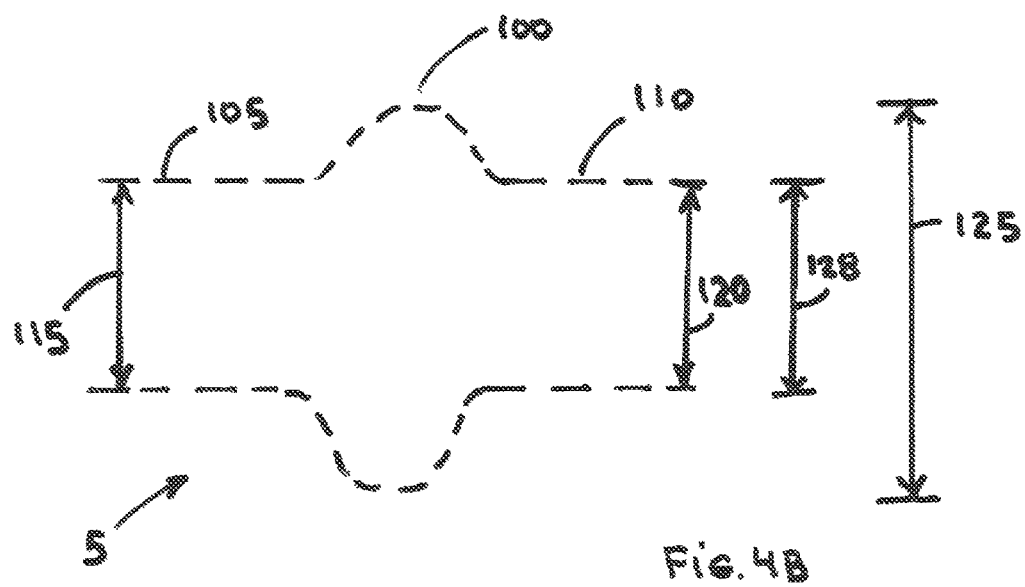
FIG. 4B

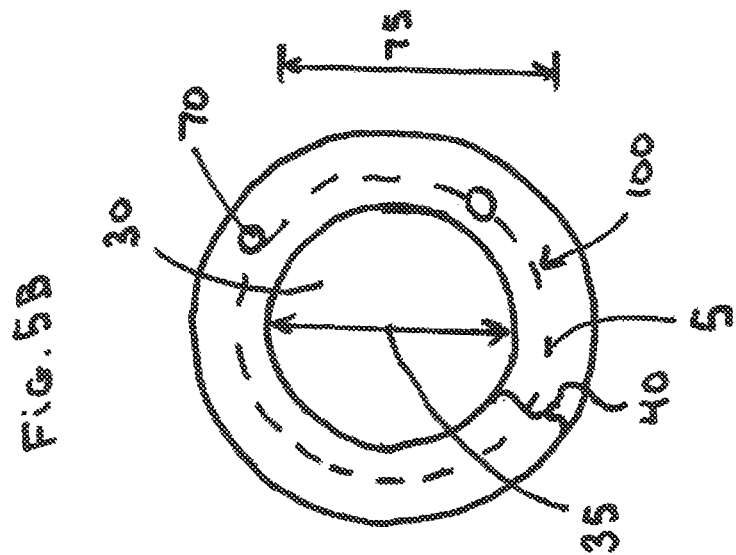
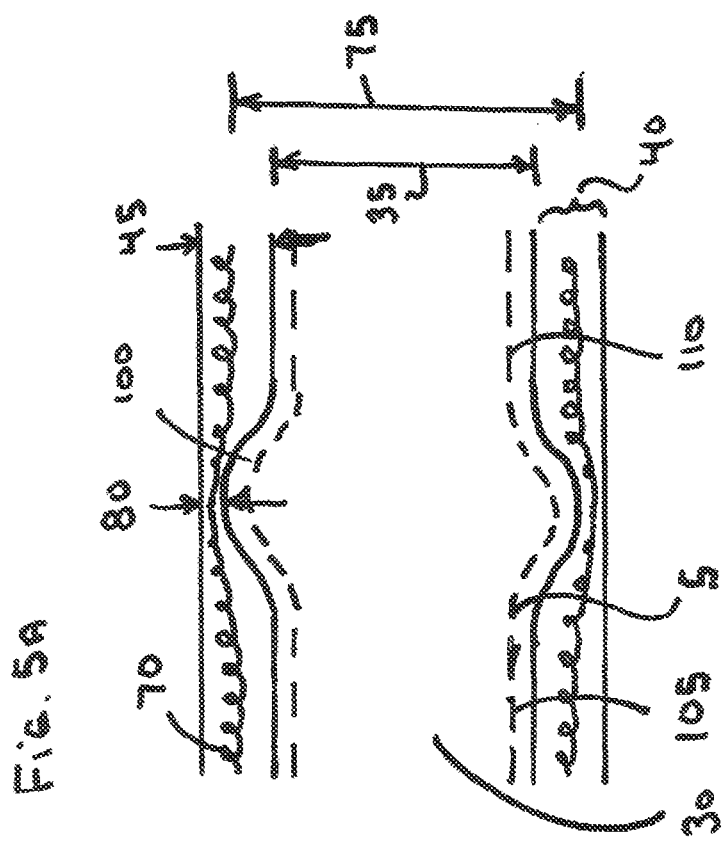

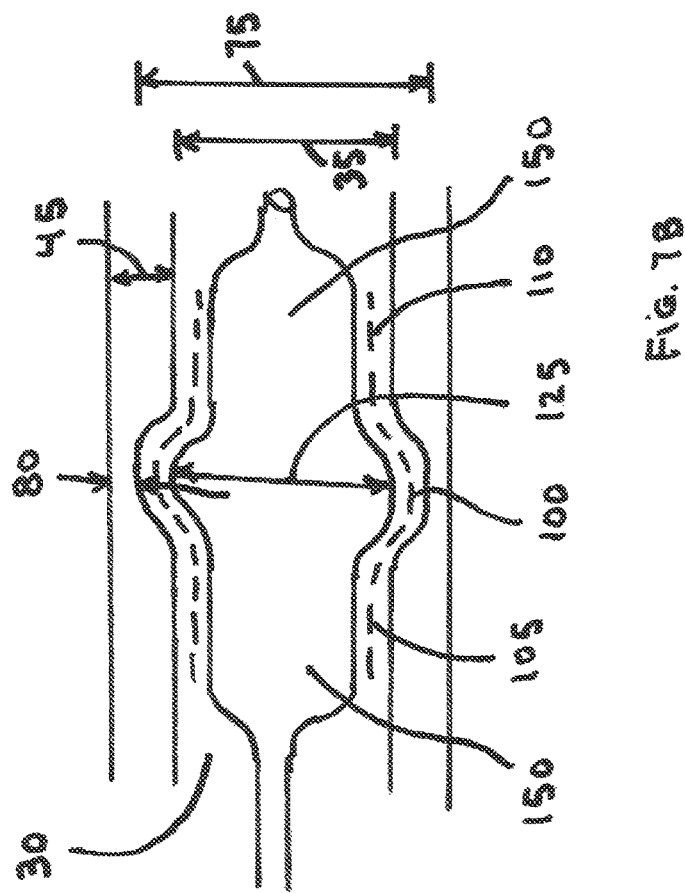
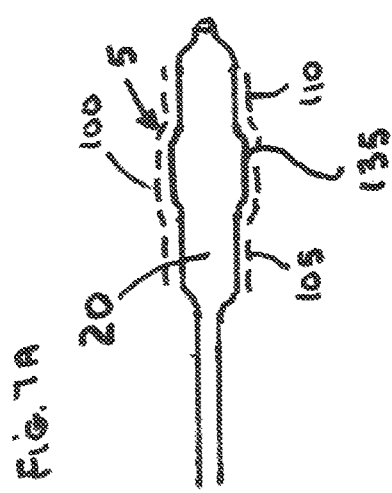

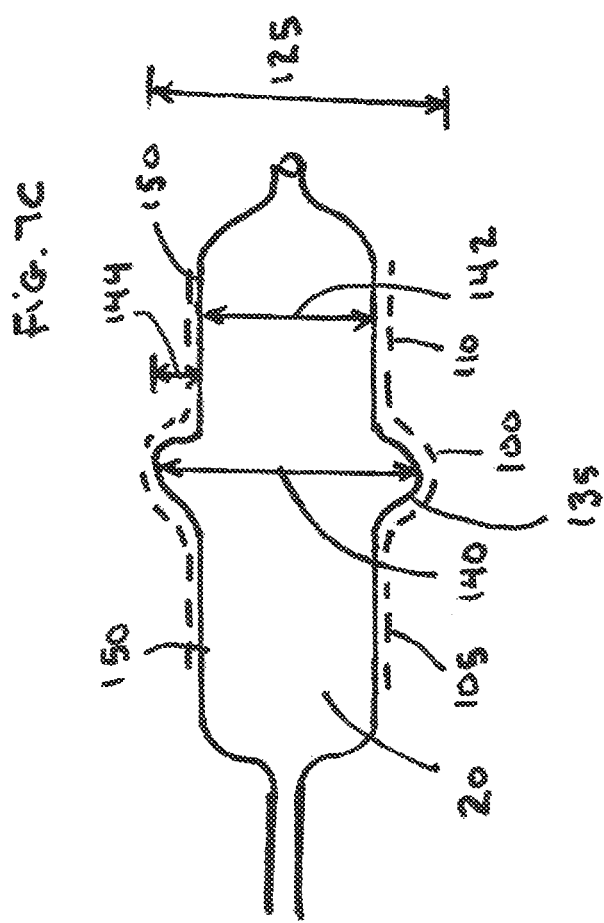

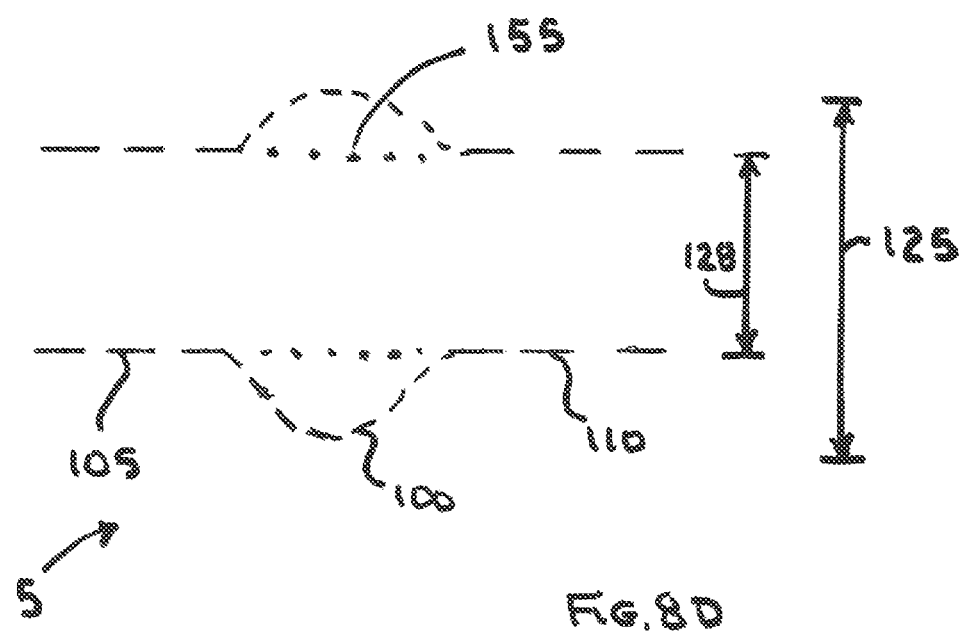

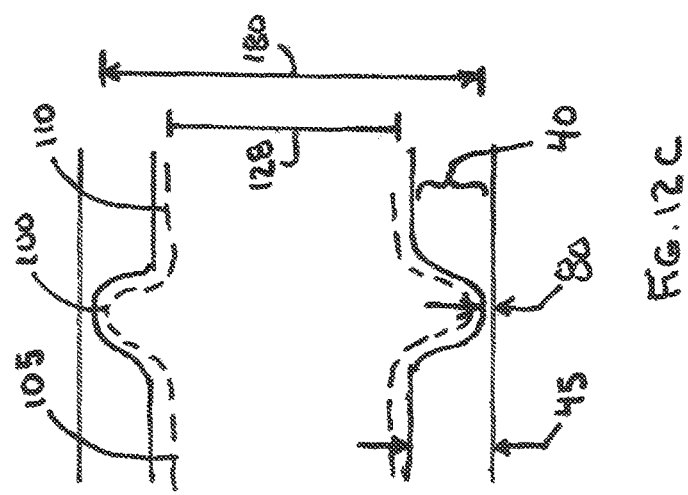
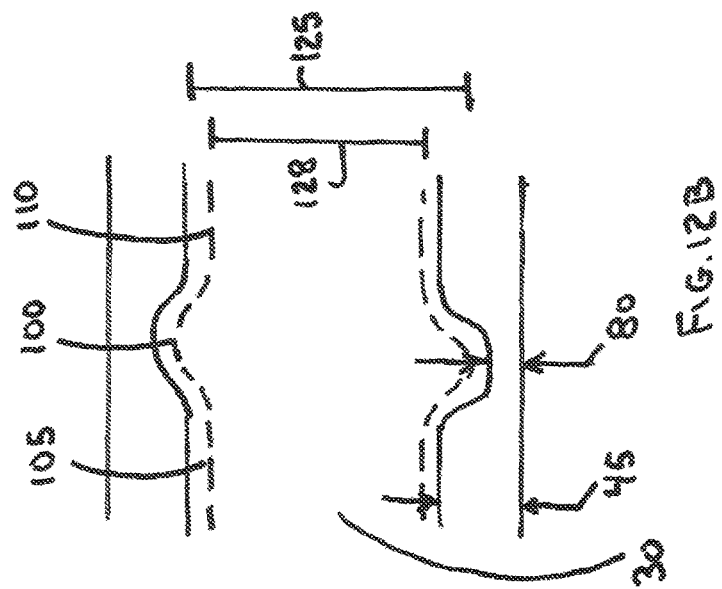
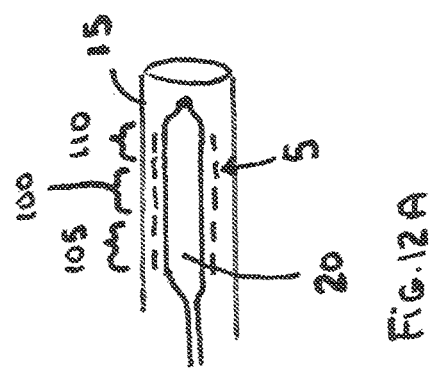

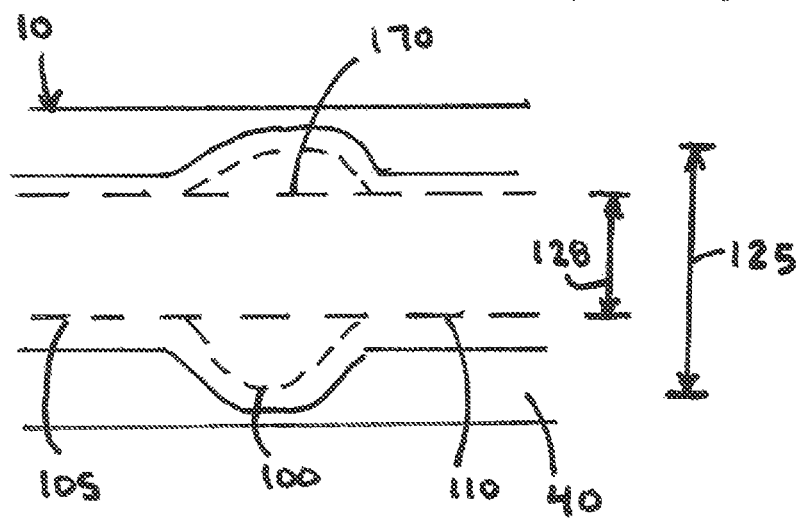
FIG. 14D
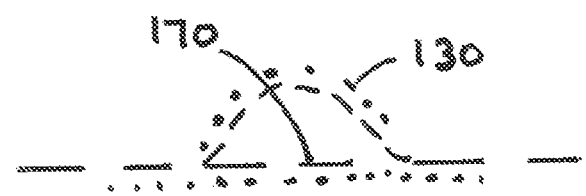
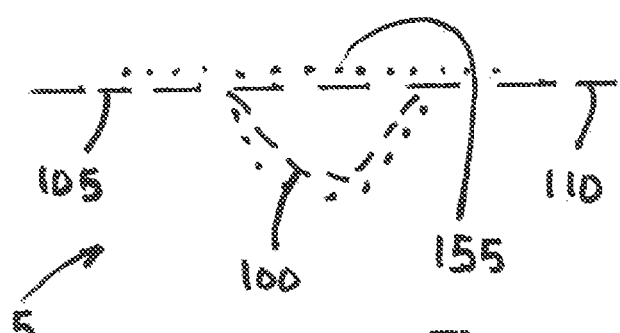
FIG. 14E

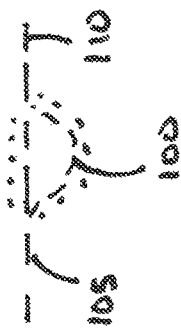
Fig. 15c
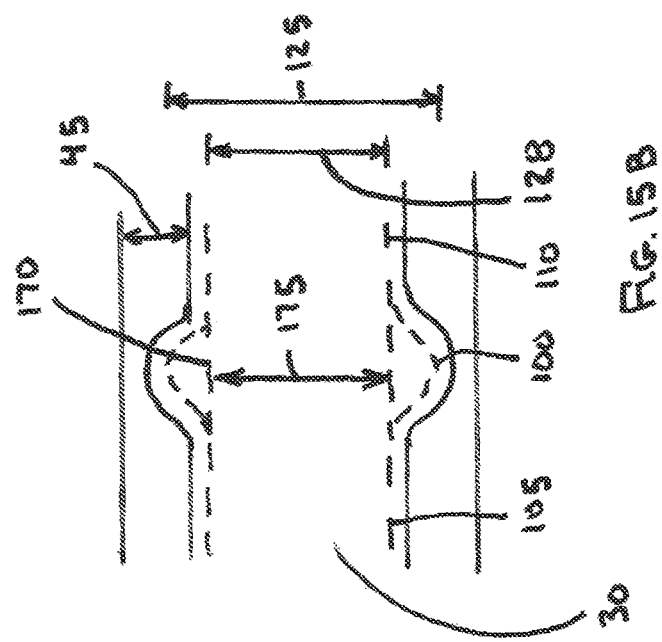
Fig. 15B
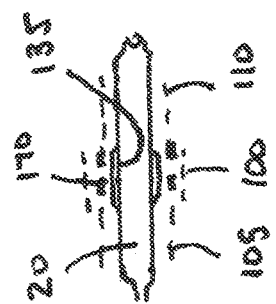
Fig. 15A

ARTERIAL WALL COMPRESSION STENT

CROSS REFERENCE TO RELATED APPLICATIONS

This patent application makes reference to and thereby incorporates all information found in the provisional patent application No. 62/285,723 entitled Arterial Wall Compression Stent, filed 6 Nov. 2015 by William J. Drasler, et. al.

BACKGROUND OF THE INVENTION

Renal Nerve Denervation (RDN) has been performed via various techniques in order to block efferent and afferent sympathetic nerve activity between the central nervous system and the kidneys and nerves that are involved with vascular control in order to treat hypertension (HTN). One technique utilizes radiofrequency (RF) energy delivered to the nerves that surround the renal arteries to cause necrosis of the nerves and hence block sympathetic signaling. The RF energy can be delivered at specific sites along a perimeter of the renal artery at a location between the renal artery ostium at the aorta and sites located near or at the junction of the renal artery with the kidneys. Various catheters with RF electrodes located along the outside of a balloon or located otherwise in contact with the arterial wall have been used to effect such RF treatment of the renal artery. Other energy means have also been utilized to affect a blockage of the sympathetic signaling including the use of ultrasound (US) and delivery of neurotoxic chemicals including alcohol directly to the wall or within the wall of the renal artery.

The problem with the current devices is that they do not deliver the energy or chemical in a uniformly distributed manner to all regions of the renal arterial wall. Some sympathetic nerves that are located near a vein or other heat sink can be shielded or otherwise protected from the thermal aspects of RF or US energy that normally would result in nerve necrosis and can therefore allow one or more of the sympathetic nerves to remain viable. Nerves located further from the sites of chemical injection will be less susceptible to necrosis and subsequent sympathetic signal blockage. Excess use of either RF, US energy or use of chemical toxins can cause the renal artery to become damaged and could result in renal artery stenosis or renal artery aneurysm, either of which can be detrimental to the patient.

What is needed is a device and method that applies a uniform pressure or uniform severing to the sympathetic renal nerves along the perimeter of the renal artery wall and throughout its wall thickness such that the sympathetic renal nerves are completely blocked around the entire perimeter and blocked to a distance from the renal artery lumen that includes all of the sympathetic renal artery nerves.

SUMMARY

The present invention is a compression stent that is intended to block sympathetic nerve signals that traverse through nerve fibers located in the walls of the renal arteries. The sympathetic nerves generally run in the adventitial layer and outer portion of the media of the renal arteries; many are located within approximately 2 mm of the arterial lumen. The compression stent can apply a compression or a pressure that causes the nerves to become compressed and thereby block nerve signal transmission. Alternately, the stent can apply a compression to the vessel wall that causes the stent to migrate through the arterial wall tissue causing the nerve to become severed or nerve signal to become disrupted as the stent frame migrates through the tissue. The compression stent can also be applied to other arteries or tubular members of the body that require a compression of the wall of the tubular member to block nerve signal transmission or for other purposes. Compression of nerves found in arteries of the body via implantation of a compression stent can also be used in the treatment of anxiety, diabetes mellitus, obesity, sleep apnea, and other disorders that have been correlated to increased sympathetic nerve activity.

Embodiments the compression stent include a self-expanding (SE) and a balloon expandable (BE) stent that applies an outward pressure onto the renal artery wall that causes a portion of the renal artery to enlarge in diameter from its initial luminal diameter by a significant amount or significant percentage of approximately 50% (range 30-100%); a 5 mm diameter renal artery, for example, could be enlarged via the compression stent to a diameter of 8 mm or larger; such significant enlargement of the renal artery diameter will cause the renal sympathetic nerves to become blocked via compression or via severance. A balloon expandable (BE) stent of the present invention can apply a compressive force upon the nerve that causes an immediate block in nerve signal transmission. A self-expanding (SE) stent which continues to grow in diameter toward an increasingly larger equilibrium diameter can cause nerve blockage immediately in some instances and over a period of hours or days in other instances.

A covering can be applied or attached to the stent frame structure to prevent the stent struts from migrating into the wall of the artery and migrate through the inner and outer elastic lamina of the artery; the presence of the covering causes the stent to apply an outward pressure to the vessel wall thereby compressing the nerve fiber and blocking the nerve signals in the wall of the renal artery. Alternately, the stent frame can be non-covered such that the enlarged diameter of the stent will cause the stent struts to migrate through the vessel wall tissue, migrate through the inner and/or outer elastic lamina, migrate into or through the nerve fiber, and ultimately cause nerve signal blockage via nerve severing or via electrical nerve signal continuity between the nerve cell interstices and the extracellular space surrounding the nerve.

In other embodiments one or more focal regions are located along a SE or BE stent such that a non-focal portion of the stent has a diameter that is similar to the diameter of the native renal artery and the focal stent regions have a diameter that is significantly larger than the luminal diameter of the native renal artery such that sympathetic nerve signals are blocked in the focal regions of the stent. The focal region with a significantly enlarged diameter will cause the arterial wall to become compressed along a circular perimeter such that a sympathetic nerve cannot extend across the focal region without becoming blocked via either compression or via severance of the nerve fibers. The focal region is located between a non-focal proximal region and a non-focal distal region of the stent frame; the non-focal regions each have a diameter that is similar to the diameter of the native artery lumen. In some embodiments for the stent the focal region has a focal region diameter that is at least 30% larger than the non-focal region diameter for either of the non-focal regions, in other embodiments the focal region diameter is at least 50% larger than the diameter of the non-focal regions, and in yet other embodiments, the focal region diameter is at least 100% larger than the diameter of the non-focal regions in an expanded configuration of the stent.

An outer focal covering can be applied to the stent in the region of the focal diameter enlargement to cause the focal region to apply a focal pressure along a perimeter of the arterial wall and block nerve conduction via external compression. The focal covering also prevents migration of cells from the arterial wall into the lumen of the compression stent resulting in stenosis of the artery. The focal covering should be formed from a material that prohibits cells from passing through its wall structure. The focal covering should in some embodiments extend into at least a portion or all of the non-focal regions of the stent to ensure that cellular migration from the artery wall into the stent lumen near the focal region is not allowed to occur. The focal covering can be formed from a thin film (approx. 0.0005 inch-0.002 inch) of porous expanded polytetrafluoroethylene (ePTFE), porous polyurethane, thin fibrous material, tissue-based materials, or other thin films that will prevent migration of the stent struts through the vessel wall as the stent places the vessel wall into a state of compression.

Alternately a focal region without an outer focal covering can apply a pressure along a perimeter that will cause the nerve fiber to become blocked via migration of the stent frame through the vessel wall tissue causing severance of the nerve fibers. The migration of the uncovered stent struts through the wall of the artery over a time period ranging from days to months. Such migration of the stent into the wall of the artery can sever the nerve fiber and disrupt the nerve transmission.

A SE embodiment of the compression stent having one or more focal regions can be formed via thermal processing of an elastomeric metal stent frame, for example, Nitinol (NiTi), such that the focal region has an equilibrium diameter that is significantly larger in diameter than other non-focal regions of the stent that have a diameter that is similar to that of the native arterial lumen diameter. In one embodiment the SE stent having the focal region with a significantly enlarged diameter can contain an inner luminal fabric or covering adjacent the focal region of the stent to form a continuous lumen diameter for the stent that forms a generally cylindrical shape having a diameter that is similar to the diameter of the native vessel lumen. The luminal fabric or covering serves to provide a generally cylindrical tubular shape across the vessel lumen adjacent the focal region of the stent extending from the proximal stent region to the distal stent region. The luminal fabric or covering can prevent thrombosis in the vessel lumen adjacent the focal region of the stent, and can reduce the ability of stenosis of the artery due to smooth muscle cell (SMC) proliferation and migration into the vessel lumen adjacent the focal region of the stent.

A BE embodiment of the compression stent having one or more focal regions can be formed from standard BE materials used for BE coronary and peripheral vascular stenting. A focal region of the stent can be formed such that it is able to expand significantly larger in diameter than a proximal and distal stent region. For example, a larger strut length or a lesser number of struts per stent length or diameter or other altered stent wall structure can be applied to the focal region of the BE stent frame to accomplish a larger attainable diameter for the focal region in comparison to other regions of the stent. To expand the BE compression stent having a focal region of significantly larger diameter will be accomplished using a dilation balloon having a balloon focal region. The balloon focal region has a diameter that is significantly (i.e., 30-100%) larger in diameter than the diameter of other remaining regions of the balloon. The balloon can be formed from standard noncompliant or semi-compliant materials used to expand standard BE stents in coronary and peripheral arterial applications. Such a balloon with a focal region is formed to retain its larger diameter focal region during expansion and deflation of the balloon. The focal region of the stent is positioned adjacent the focal region of the balloon during the delivery of the catheter through the vasculature and during expansion of the compression stent, the delivery catheter is positioned such that the focal regions of the balloon and stent are adjacent the region of the native renal artery that has the sympathetic nerves that are intended to be blocked. Expansion of the balloon will expand the focal region of the stent out into compressive contact with the renal artery causing the wall of the renal artery to compress and causing the renal sympathetic nerves to become blocked. A focal covering can be bonded or attached to the focal region of the BE stent. The focal covering can be formed from a thin film of porous expanded polytetrafluoroethylene (ePTFE), porous polyurethane, thin fibrous material, tissue-based materials, or other thin films that will prevent migration of the stent struts through the vessel wall. Alternately, a focal covering need not be applied to the focal region of the compression stent to allow the stent struts to migrate through the vessel wall tissue and cause severance of the sympathetic nerve fibers. A luminal covering can be attached to the proximal and distal stent regions of the compression stent and located within the lumen of the blood vessel; the luminal covering has a diameter that is similar to the diameter of the proximal and distal regions of the stent. The luminal fabric or covering of this embodiment must be able to expand during expansion of the focal region of the balloon and then rebound back to a diameter that matches the diameter of the native vessel. This luminal covering can be formed from an elastomeric film such as microporous polyurethane (PU) or other elastomeric polymer. The luminal covering can be joined to the proximal and distal stent regions. The luminal covering will prevent thrombosis and reduce the likelihood for SMC proliferation and migration into the vessel lumen adjacent the focal region of the stent.

In yet another embodiment the SE compression stent can be formed such that it has a focal region that makes compressive contact with the wall of the tubular member or vessel of the body and compresses the wall tissue of the vessel and also a luminal stent region that extends in a cylindrical manner with the same diameter as the lumen of the native vessel. The luminal stent can be joined, for example, to SE proximal and distal regions of the stent via various bonding, attaching or welding techniques or can be formed contiguously via 3D machining techniques. The entire stent, including the luminal stent region can be formed from SE materials using thermal processing to form specific focal regions with a larger diameter than a non-focal region diameter. The focal region and/or luminal stent region can have a covering attached to them to provide benefits as described earlier.

In further other embodiments the compression stent can be formed such that the proximal and distal regions are formed from a BE material and the focal region is formed from a SE material. The BE portions of the stent allow the compression stent to be mounted onto a dilation balloon. The dilation balloon can be either cylindrical in shape or it can be a focal balloon with the focal balloon region of significantly larger (i.e., 50% larger, range 30-100%) focal region diameter than the diameter of non-focal regions of the balloon. The focal region of the balloon is positioned adjacent the SE focal region of the compression stent. Upon release of the balloon mounted stent from the sheath, the SE focal region expands outwards. The balloon can then be expanded to dilate the BE non-focal regions of the compression stent. In one embodiment a cylindrical balloon will dilate the BE proximal and distal regions of the compression stent to match the diameter of the native artery while the SE focal region is designed to expand significantly larger than the native artery and expand to its fullest extent over a time period of minutes to days. In another embodiment a balloon with a focal region that is positioned adjacent to the SE focal region of the stent allows the focal region of the stent to expand outwards to the fullest extent of the balloon focal region diameter immediately and affect a blockage of all sympathetic nerves. Even after deflation and removal of the dilation balloon additional expansion of the SE focal region will further cause compression or severance of the sympathetic nerves as it reaches the stent focal region full equilibrium diameter; this phenomenon is observed clinically with the SE TAVR stent valves which often can cause bundle branch block in the heart after implantation of the device. The compression stents of these embodiments can also contain a focal covering and/or a luminal covering. The compression stents of these embodiments also can contain a luminal stent located adjacent the focal stent region and having a diameter that is similar in diameter to the native artery lumen diameter.

Drugs can be used with any of the embodiments of the present invention to enhance their effectiveness; such drugs can be placed onto the focal region of the stent, the proximal or distal regions of the stent, the luminal stent, the focal covering, or the luminal covering, or any covering located on the stent. For example, anti-proliferative drugs such as Taxol or Sirolimus can be used to prevent cellular proliferation and migration into the luminal region that could lead to vessel stenosis. Also, antithrombotic agents can be placed onto the compression stent device to reduce thrombosis in the lumen region of the vessel adjacent the focal region of the stent. Other drugs including alcohol or nerve blocking or necrotic agents such as alcohol can be applied to any portion of the present invention to assist in causing nerve blocking.

The compression stent of the present invention can be formed from a material that allows the stent frame to be heated up via an external application of energy including RF, US, focused US, microwave, other electromagnetic energy form, magnetic coupling, IR light, UV light or other energy forms. For example, if the nerve fibers were not entirely blocked along a perimeter of the renal artery, energy could be delivered to the stent, absorbed by the stent, and cause the stent to increase in temperature resulting in further trauma to the sympathetic nerves of the renal artery, and provide additional therapeutic benefit by further blocking sympathetic nerve transmission. The stent could be designed such that it contains, for example, a coil that interacts with an external magnetic field that allows it to be heated noninvasively via energy coupling to the coil at an energy frequency that is characteristic to the coil energy absorption frequency.

The compression stent of the present invention can be formed with a circuit that is able to detect continuity of electrical conduction through the wall of the renal artery. The circuit can be probed initially during implant of the compression stent to determine if the sympathetic nerve signal has been blocked. If the nerve signal is not blocked, further dilation of the stent can be performed prior to exiting the interventional access site during the interventional procedure. If the stent is probed externally at a later time, it can be determined if the nerve blockage has been durable. If the blockage is not durable, then further dilation of the stent can be accomplished or else a noninvasive thermal heating of the stent via an external energy means can be utilized.

BRIEF DESCRIPTION OF THE DRAWINGS

FIG. 1E is a longitudinal section view of a blood vessel with a compression stent located along the lumen of the blood vessel.

FIG. 1F is a cross-sectional view of a blood vessel with a compression stent located along the lumen of the blood vessel causing the blood vessel wall to become compressed.

FIG. 1G is a cross-sectional view of a blood vessel showing a compression stent that has migrated into the vessel wall and causing trauma to the nerve.

FIG. 2C is a longitudinal view of an inflated compression stent located on an inflated dilation balloon.

FIG. 2D is a cross-sectional view of a blood vessel with a compression stent located on its lumen and causing the blood vessel wall to become compressed and causing trauma to the nerve.

FIG. 3 is a longitudinal sectional view of a compression stent having a covering attached to a surface of the compression stent.

FIG. 4A is a longitudinal view of a compression stent having a self-expanding stent focal region and self-expanding non-focal regions; the compression stent is held in a nonexpanded configuration by an external sheath.

FIG. 4B is a longitudinal view of a compression stent with a self-expanding stent focal region and self-expanding non-focal regions that has been released from an external sheath to its expanded configuration.

FIG. 5A is a longitudinal sectional view of a blood vessel having a compression stent located in the vessel lumen and causing the vessel wall to become compressed further causing trauma to a nerve.

FIG. 5B is a cross-sectional view of a blood vessel having a compression stent located in the vessel lumen and causing the vessel wall to become compressed further causing trauma to the nerves.

FIG. 7A is a longitudinal view of a balloon expandable compression stent having a stent focal region in a nonexpanded configuration mounted onto a dilation balloon having a balloon focal region.

FIG. 7B is a longitudinal view of a balloon expandable compression stent having a stent focal region in an expanded configuration mounted onto a dilation balloon having a balloon focal region; the stent focal region has compressed the wall of a blood vessel.

FIG. 7C is a longitudinal view of a balloon expandable compression stent having a focal region that grows in diameter at a greater rate relative to the non-focal regions.

FIG. 8D is a longitudinal view of an expanded compression stent having a focal stent region and having a luminal covering located between the non-focal regions and having the same diameter as the non-focal regions.

FIG. 12A is a longitudinal view of a compression stent having a self-expanding focal region and balloon expandable non-focal regions; the compression stent is mounted onto a dilation balloon and is held in an nonexpanded configuration by an external sheath.

FIG. 12B is a longitudinal view of a compression stent having a self-expanding focal region and balloon expandable non-focal regions; the compression stent has been released from an external sheath and a dilation balloon has expanded the balloon-expandable regions.

FIG. 12C is a longitudinal view of a compression stent having a self-expanding focal region and balloon expandable non-focal regions; the compression stent has been released from an external sheath and a dilation balloon has expanded the balloon-expandable regions; the stent focal region has expanded further over time.

FIG. 14D is a longitudinal view of a compression stent in an expanded configuration; the focal stent region has a focal covering, the luminal stent has a luminal covering.

FIG. 14E is a longitudinal view of a compression stent having a luminal stent with a luminal covering and a stent focal region with a focal covering.

FIG. 15A is a compression stent having a balloon expandable focal region and non-focal regions; the compression stent has a self-expanding luminal stent; the compression stent is mounted onto a dilation balloon having a balloon focal region.

FIG. 15B is a compression stent having a balloon expandable focal region and non-focal regions; the compression stent has a self-expanding luminal stent; the compression stent is in an expanded configuration.

FIG. 15C is a compression stent having a balloon expandable focal region and non-focal regions; the compression stent has a self-expanding luminal stent; the compression stent is in an expanded configuration; a covering is located on the stent focal region and the luminal stent.

DETAILED DESCRIPTION

Figure 1A:
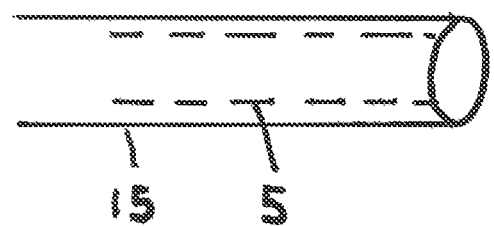
FIG. 1A is a longitudinal section view of an embodiment of a self-expanding compression stent in a nondeployed configuration held by an external sheath.
Figure 1B:
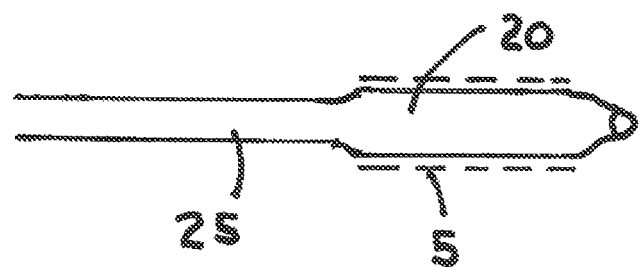
FIG. 1B is a longitudinal section view of an embodiment of a balloon expandable compression stent in a nondeployed configuration mounted on a dilation balloon.

FIGS. 1A-1F show embodiments of a compression stent (5) that is being deployed into a renal artery (10), for example, or other tubular member of the body. The compression stent (5) can be a self-expanding (SE) stent that is held into a small diameter configuration via an external sheath (15) as shown in FIG. 1A. Alternately, the compression stent (5) can be a balloon expandable (BE) stent that is mounted onto the outside of a dilation balloon (20) that is located at the distal end of a balloon dilation catheter (25) as shown in FIG. 1B. As a BE stent, the compression of the nerve and blockage of the nerve signal can be observed very quickly, either immediately or within minutes after implantation of the stent. If the compression stent (5) is formed from with a SE character, the blockage of the nerve signal often will occur within a period of time ranging from minutes to hours to days after implantation of the compression stent. The SE compression stent will continue to grow in diameter after the immediate implantation diameter towards its equilibrium diameter (as found for the SE stent in free space) and thereby result in nerve blockage as observed in the clinic, for example, with SE stented valves that are placed on or near the aortic annulus in TAVR procedures.

Figure 1C:
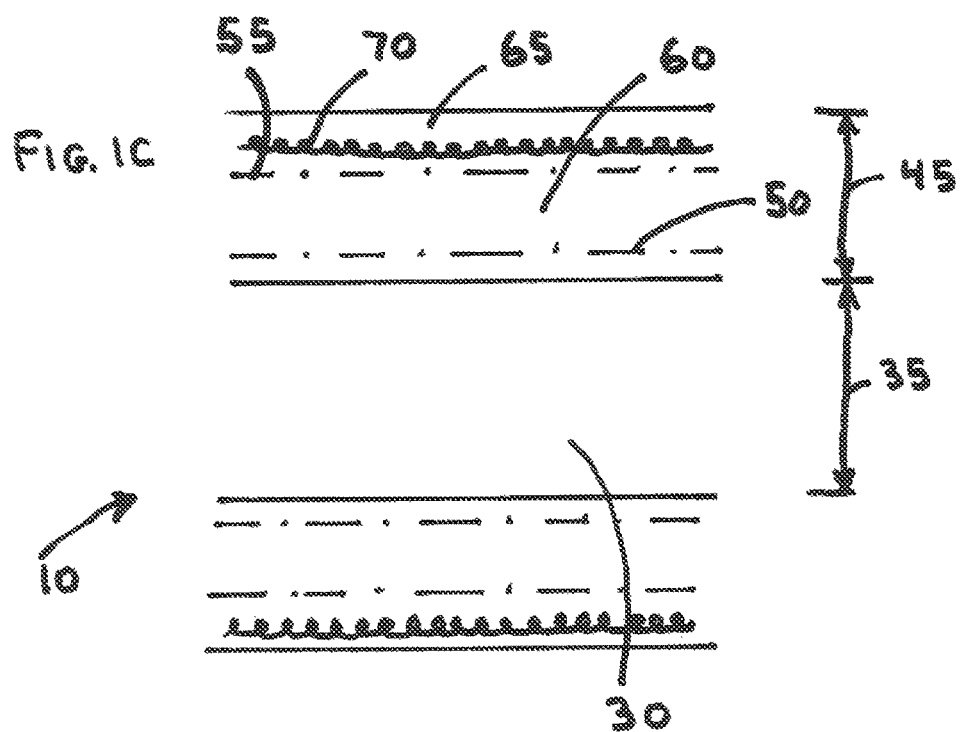
FIG. 1C is a longitudinal section view of an arterial blood vessel.
Figure 1D:
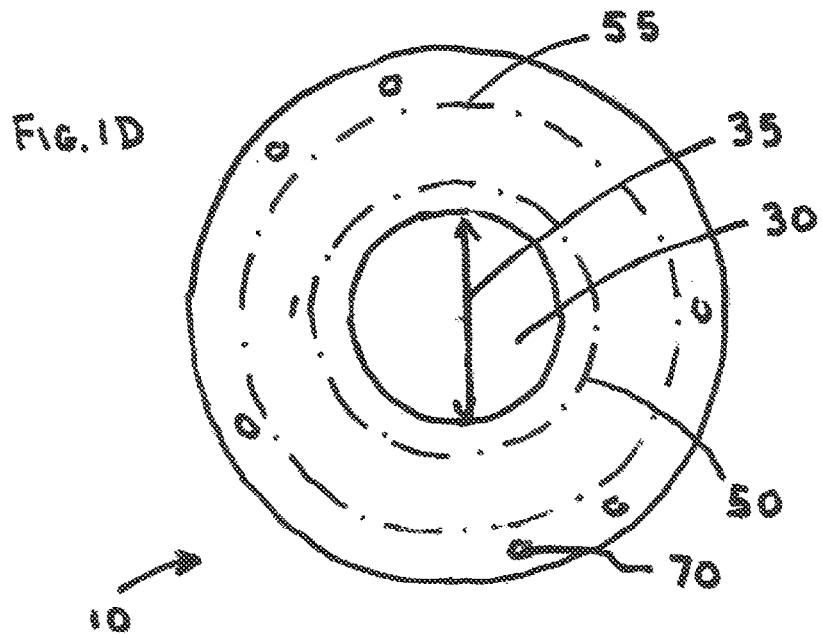
FIG. 1D is a cross-section of an arterial blood vessel.

The artery (10) as shown in FIGS. 1C and 1D has a vessel lumen (30) with a native lumen diameter (35) and a vessel wall (40) with a native wall thickness (45). The vessel wall has an inner elastic lamina, IEL (50) and an external elastic lamina, EEL (55); located between the IEL (50) and EEL (55) is a medial layer (60). Outside of the EEL (55) is the adventitial layer (65) in which most of the sympathetic nerves (70) reside. The nerves (70) extend through the adventitial layer (65) as well as the outer layers of the media extending along in the axial direction of the artery. Upon release of the SE compression stent (5) or BE compression stent (5) into the vessel and into its expanded state, the compression stent (5) causes the vessel to expand in diameter to a significantly larger (i.e., 30-100% larger than its native lumen diameter (35)) expanded lumen diameter (75) and compresses the adventitial layer (65) that contains the sympathetic nerve fibers (70) to a smaller compressed wall thickness (80) as shown in FIGS. 1E and 1F. The compression of the nerve fibers can lead to blockage of nerve signal transmission through the nerve fibers. For a stent that is not provided with a covering material as seen in FIG. 1G, the stent struts can migrate through the vessel wall and sever the nerve fibers causing a loss of sympathetic nerve signaling.

Figure 2B:
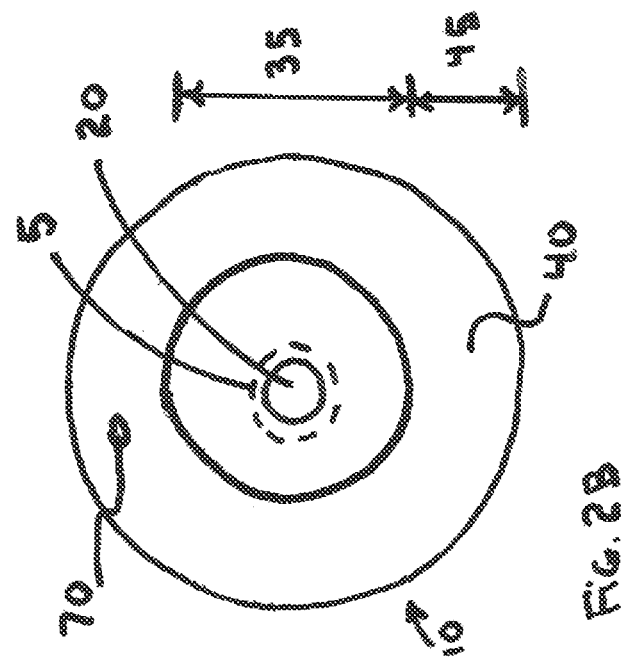
FIG. 2B is a cross-sectional view of blood vessel with a compression stent located on a noninflated dilation balloon that is in the vessel lumen.
Figure 2A:
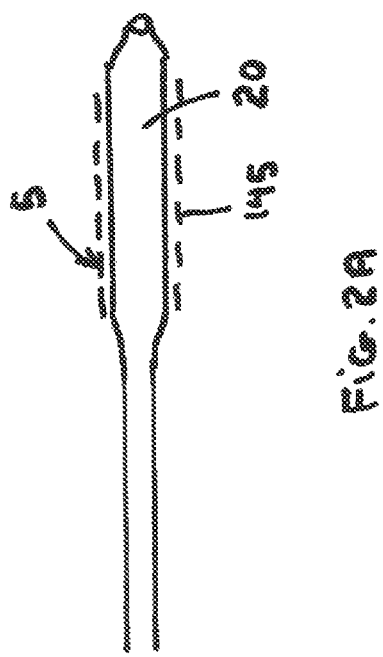
FIG. 2A is a plan view of a dilation balloon in a noninflated configuration with a compression stent located on the balloon.

FIGS. 2A-2B show a BE compression stent (5) being inserted in its nondeployed or nonexpanded configuration into a native arterial vessel or tubular member of the body. The vessel has a native lumen diameter (35) and a native wall thickness. Upon expansion of the dilation balloon (20) (FIGS. 2C and 2D) to a significantly larger (i.e., the balloon is 50% larger, range 30-100% larger than the native lumen diameter) inflated balloon diameter (85), the compression stent (5) causes the blood vessel or artery (10) to enlarge in diameter to a significantly greater expanded lumen diameter (75) and the native wall thickness thins down to a smaller thickness. Nerves (70) that are found in the vessel wall will become compressed and are exposed to severance via the stent struts of the compression stent (5). The severance of such nerves (70) can provide a therapeutic benefit in the treatment of hypertension (HTN).

FIG. 3 shows either a BE or SE compression stent (5) having a stent covering (90) that is attached or bonded to the stent frame structure (95), the stent frame structure being defined by its geometric design and stent pattern that forms the compression stent. A separate name and reference numeral will be presented for the stent covering (90) that is located in various regions of the compression stent (5). The stent frame being comprised of hinges (or bent regions), struts (or straight regions that join bent regions), connectors (that connect rings of stent frame members together), and other structures that form the stent frame. The covering (90) can be thin film of ePTFE, microporous PU, microporous polyethylene terephthalate (PET), nylon, or other microporous polymeric material, or tissue material that will prevent the stent frame structure (95) from migrating through the vessel wall tissue, but will allow for tissue ingrowth for healing of the compression stent (5) and covering (90) to occur. The material can be noncompliant or can be semi-compliant material. The covering (90) can be attached to the stent frame via sutures, adhesives, thermal bonding, and encasement of the stent within two layers of covering (90) or via other attachment means.

One embodiment of the present compression stent (5) invention as shown in FIGS. 4A and 4B is a SE stent that contains a stent focal region (100) positioned between a stent proximal region (105) and a stent distal region (110); the stent proximal region (105) and stent distal region (110) can collectively be referred to as the stent non-focal regions (152). FIG. 4A shows the stent in a nonexpanded configuration contained within an external sheath; FIG. 4B shows the stent in an expanded state. The proximal region diameter (115) and distal region diameter (120) are approximately equal to the native lumen diameter (35) of the native artery (10), although a small oversizing of the stent from zero to 15% for the non-focal regions can be made relative to the native lumen diameter. The stent focal region (100) has a stent focal region diameter (125) that is approximately 50% larger (range 30-100% larger) than the native lumen diameter (35) and approximately 50% larger (range 30-100%) than the stent non-focal region diameter (128), the stent non-focal region diameter being an average of the stent proximal region diameter (115) and the stent distal region diameter (120). The stent proximal region (105) and stent distal region (110) can be attached to the stent focal region (100) via bonding, welding, soldering or other process methods; alternately the stent regions can be formed contiguously with each other via standard mechanical, laser machining methods, thermal processing methods, or other processing methods including machining all regions of the stent frame from a single metal tube, for example. The outward pressure provided by the stent focal region (100) against the vessel wall is approximately equivalent to a dilation balloon (20) placed inside the lumen of the artery (10) and inflated to 6 atm (range 5-10 atm). More than one stent focal region (100) can be contained in the compression stent; one or more non-focal regions (for example, the proximal and distal regions) can be located anywhere adjacent axially to the one or more stent focal regions. The presence of the focal region allows a greater applied pressure (force/area) to be applied to the vessel wall owing to a smaller area of applied force located in the focal region alone. This greater applied pressure allows the vessel wall to undergo a greater compression pressure along a perimeter of the vessel wall resulting in either a severance of the nerve fibers via the stent frame or via compression of the nerve fiber and loss of signal transmission through the nerve fiber.

As shown in FIGS. 5A and 5B the SE compression stent (5) of this embodiment is formed with the stent proximal region (105), stent distal region (110), and stent focal region (100) constructed from an elastic metal such as Nitinol, Elgiloy, for example. The compression stent (5) has a stent focal region (100) that is applying a large pressure onto the nerve fiber; the vessel or artery (10) has enlarged in its expanded lumen diameter (75) adjacent to the stent focal region (100) from its native lumen diameter (35) to a significantly larger expanded lumen diameter (75), and the vessel native wall thickness has thinned down to a compressed wall thickness. The nerve fiber has been severed by a strut of the stent frame and caused the nerve fiber to lose sympathetic transmission; another nerve fiber has been compressed and has lost its ability for sympathetic nerve transmission.

Figure 6A:
FIG. 6A is a longitudinal view of a compression stent in an expanded configuration having a stent focal region and having a covering attached to the stent surface.
Figure 6B:
FIG. 6B is a longitudinal view of a compression stent in an expanded configuration having a focal region and having a covering that is attached to the surface of the focal region.
Figure 6C:
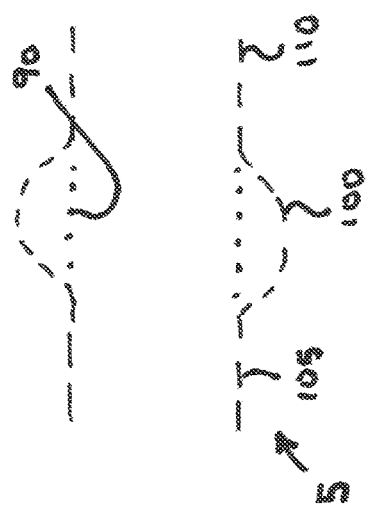
FIG. 6C is a longitudinal view of a compression stent in an expanded configuration having a focal region and having a luminal covering that is not attached to the surface of the focal region; the luminal covering does not grow in diameter as the focal region grows in diameter.

A covering (90) can be applied via attachment, suturing, adhesive bonding, encapsulation, or other methods to the compression stent (5) over its entire surface as shown in FIG. 6A in an expanded state or only in the focal region of the stent forming a focal region covering (130) as shown in FIG. 6B. The presence of a covering (90) that is attached to the wall of the compression stent will allow the compression stent (5) to compress the vessel wall tissue without migration of the stent frame or stent struts (145) through the tissue. The covering can be a porous material such as found in a vascular graft to allow cellular tissues to penetrate the covering and provide a healing capability to the tissues that reside on the luminal side of the covering. The pressure applied to the nerve fiber via the focal region of the stent will cause the nerve fiber to compress in its cross section and will cease to transmit sympathetic signals. Alternately, the covering can reside on the inner surface of the stent as shown in FIG. 6C and can remain unattached to the stent wall in the stent focal region. As the stent focal region grows outwards to a significantly larger diameter than the native lumen diameter, the covering located in the stent focal region can become a luminal fabric or covering and can remain in a cylindrical shape that is equal to the stent non-focal region diameter to function as a cellular infiltration resistance; the luminal covering will help to reduce thrombosis due to blood stagnation in the region of the blood vessel lumen that has been expanded in diameter and the luminal covering will help to reduce hyperplastic cellular growth and infiltration into the lumen of the blood vessel between the non-focal regions. The luminal covering or stent focal covering can extend a small distance axially of a few millimeters into the non-focal regions to prevent cellular infiltration.

A BE compression stent (5) can be formed such that the stent proximal region, stent distal region, and stent focal region (100) are all formed from balloon expandable materials such as stainless steel, titanium, and other materials used to form vascular stents. The compression stent (5) can be delivered to the renal artery (10) via a dilation balloon (20) that has a balloon focal region (135) as shown in FIGS. 7A and 7B. The stent focal region (100) is mounted onto the dilation balloon (20) adjacent the balloon focal region. The balloon focal region (135) is formed into the balloon during the balloon blowing process and focal shape of the balloon is retained during balloon inflation. The balloon can be formed from materials including PET, Nylon, Pebax, and other noncompliant and semicompliant materials used in therapeutic balloons for angioplasty. Upon dilation of the balloon, the balloon focal region (135) dilates the stent focal region (100) to a stent focal region diameter (125) that is significantly (i.e., 50% larger, range 30-100% larger) larger than the vessel native lumen diameter (35) and significantly larger than the balloon non-focal regions (150) and significantly larger than the stent non-focal region diameter (128) putting the stent into an expanded state. The vessel wall thickness adjacent the stent focal region (100) has been thinned down to a compressed wall thickness (80) that is smaller than the vessel native wall thickness and causes the nerve fiber to be compressed. The stent struts (145) can migrate through the nerve fiber causing the nerve to sever and lose its transmission capability. The balloon non-focal regions (150) are located adjacent to the stent non-focal regions (152); the balloon non-focal regions (150) extend the stent non-focal regions (152) to a stent non-focal region diameter (128) that is approximately the same as the native lumen diameter (35) with minimal oversizing of the stent non-focal regions (152) by zero to 15% larger than the native lumen diameter.

As shown in FIG. 7C, the balloon non-focal region (150) can be formed with a balloon material that is more noncompliant than the balloon focal region (135) or the balloon non-focal regions are formed using an outer wrap of small diameter multifilament polyethylene terephthalate fibers, for example, such that the non-focal regions (150) are not able to expand in diameter as much as the balloon focal region (135) as the inflation balloon (20) inflation pressure is increased. Increasing the balloon inflation pressure will allow the balloon focal region (135) and the stent focal region (100) to grow in diameter under increasing inflation balloon (20) inflation pressure until a blockage in nerve signal is observed without negatively dilating or imposing trauma onto the native artery on either side of the stent focal region (100). The balloon focal diameter (140) for this embodiment grows at a greater rate than the balloon non-focal diameter (142) such that the relative stent focal to non-focal diameter (144) increases with increased inflation pressure in the dilation balloon (20).

Figure 8B:
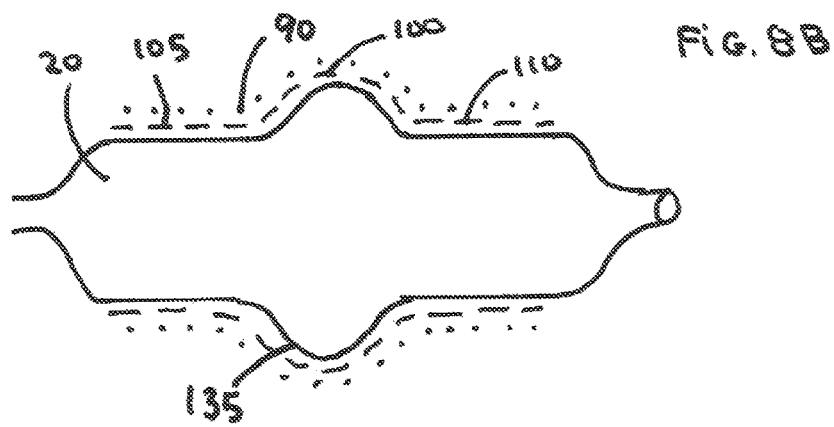
FIG. 8B is a longitudinal view of a balloon expandable compression stent with a stent focal region in an expanded configuration positioned onto a dilated balloon having a balloon focal region that is inflated to a pressure ranging from 1-3 atm; a covering is attached to the surface of the stent.
Figure 8A:
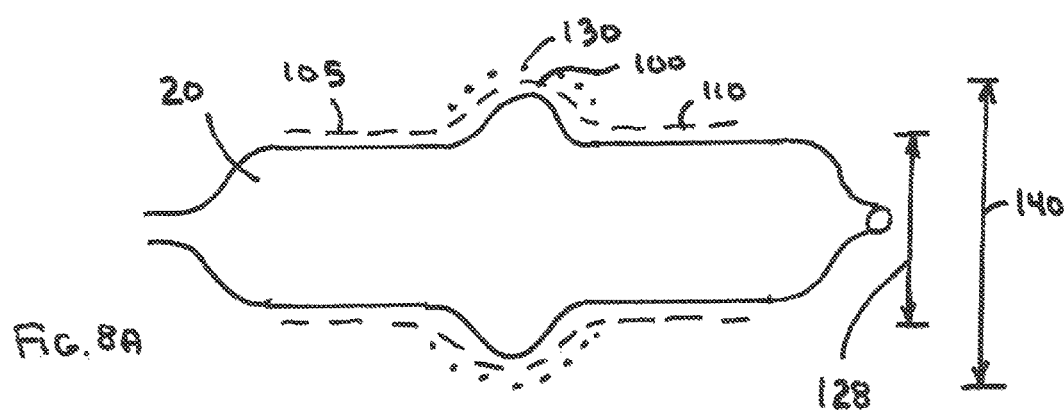
FIG. 8A is a longitudinal view of a balloon expandable compression stent with a stent focal region in an expanded configuration positioned onto a dilated balloon having a balloon focal region; a covering is attached to the stent focal region.
Figure 8C:
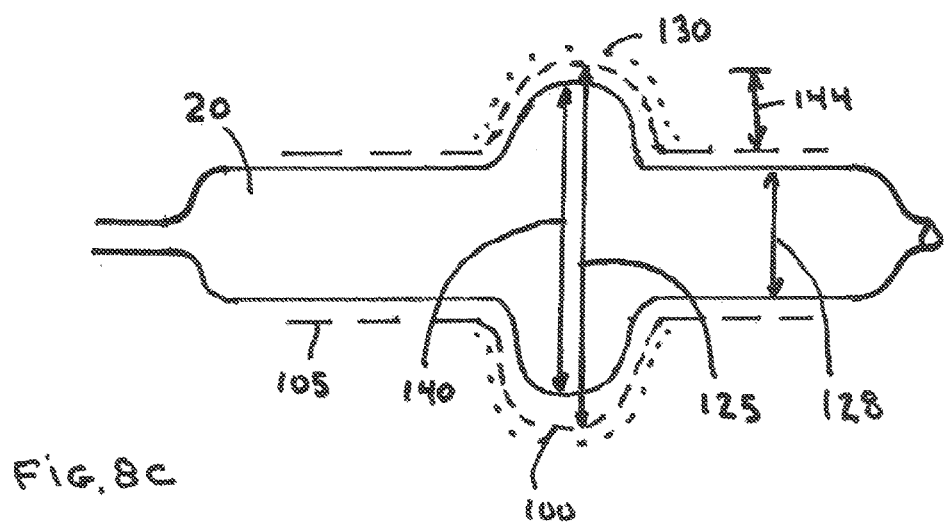
FIG. 8C is a longitudinal view of a balloon expandable compression stent with a stent focal region in an expanded configuration positioned onto a dilated balloon having a balloon focal region that is inflated to a pressure ranging from 4-12 atm; a covering is attached to the surface of the focal region.

The stent covering (90) can be attached along the entire stent structure as shown in FIG. 8A as the balloon is inflated. A stent focal region covering (130) can be attached or bonded onto the compression stent (5) to prevent migration of the stent focal region (100) through the vessel wall as the inflation balloon is inflated to a pressure ranging from 1-3 atm and the focal region reaches a diameter ranging from 30-100% greater than the native lumen diameter as shown in FIG. 8B with the stent in an expanded state. The focal dilation balloon can be further inflated to a larger pressure ranging from 3-12 atm to cause the focal region of the balloon and the focal region of the stent to grow further in diameter of up to 200% of the native lumen diameter. As shown in FIG. 8C, the balloon focal region diameter (140) can be increased at higher balloon inflation pressures to cause the stent focal region diameter (125) to increase a greater diametric amount relative to the stent non-focal diameter (128) thereby generating a greater relative stent focal to non-focal diameter (144). To provide for relative growth of the balloon focal region the focal dilation balloon can be formed with a balloon focal region that is either a compliant material such as polyurethane or a semicompliant material Nylon or Pebax. The non-focal regions can be supported with an external layer of noncompliant polymeric material such as polyethylene terephthalate, a braid, or other supported structure to prevent the non-focal regions of the balloon from undergoing diametric growth at the higher pressures as described. The focal dilation balloon can then be inflated to increasing pressures until notation is made by the operator that the nerve conduction signals have been blocked via vessel wall compression or via nerve severance from the compression stent.

A luminal fabric or luminal covering (155) can also extend from the stent proximal region (105) to the stent distal region (110) across the stent focal region (100) to form a cylindrical luminal fabric or luminal covering (155) adjacent to the stent focal region (100) as shown in FIG. 8D and can extend into the non-focal regions. This luminal covering (155) can prevent thrombosis form occurring in the vessel lumen (30) due to the greater luminal diameter provided by the stent focal region. The luminal fabric or luminal covering (155) also assists in blocking smooth muscle cell migration or cellular hyperplasia into the vessel lumen (30) adjacent the stent focal region. The luminal fabric or luminal covering (155) for the BE compression stent (5) having a stent focal region (100) that is expanded outwards via the balloon focal region (135) requires a luminal covering (155) that is elastic in character such that it can expand during inflation of the balloon focal region (135) and can rebound back to a native lumen diameter (35) after the dilation balloon (20) has been deflated. The luminal fabric or luminal covering (155) can be formed from a microporous PU, fibrous PU, silicone, or other microporous elastomeric polymeric material.

Figure 9B:
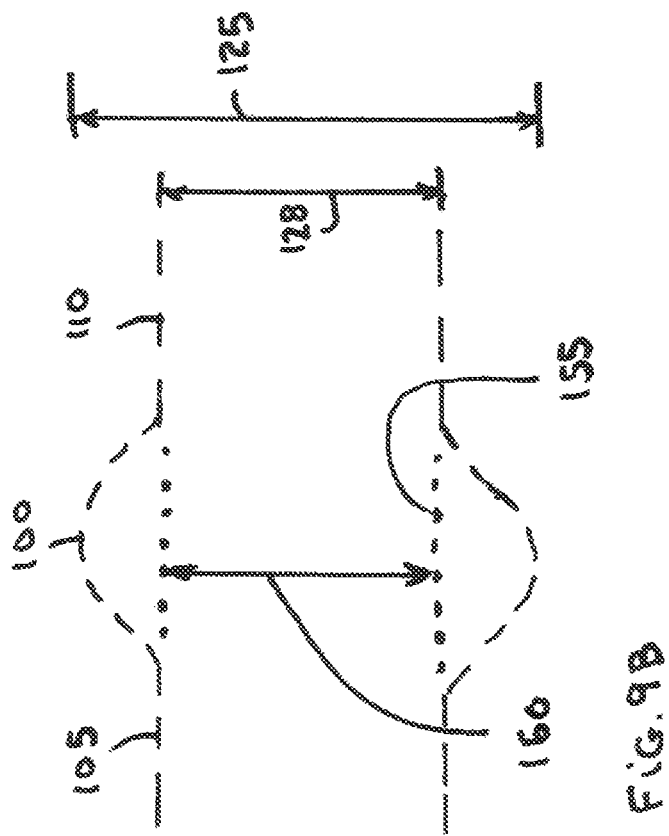
FIG. 9B is a longitudinal view of a self-expanding compression stent held in an expanded configuration; the compression stent has a luminal covering extending between the stent non-focal regions.
Figure 9A:
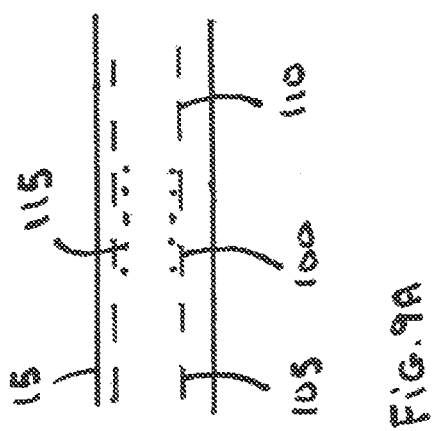
FIG. 9A is a longitudinal view of a self-expanding compression stent held in a nonexpanded configuration within an external sheath; the compression stent has a luminal covering near the focal stent region.

In one embodiment a SE compression stent (5) having a stent focal region (100) can also contain a luminal covering (155) as shown in FIGS. 9A and 9B. The luminal covering (155) is attached or bonded to the stent proximal region (105) and to the stent distal region (110) and forms a cylindrical tube across the stent focal region (100) having a luminal fabric diameter (160) or luminal covering diameter (160) that is the same as the stent non-focal region diameter (128); the luminal fabric or luminal covering (155) can extend into the proximal non-focal region (105) and distal non-focal region (110). This embodiment is released from an external sheath and expands outwards to an expanded state such that the stent non-focal region reaches a stent non-focal region diameter (128) that is similar to the native lumen diameter (35) with a small oversizing of the stent non-focal regions (152) such that they are zero to 15% larger than the native lumen diameter. The focal stent region expands outwards to a significantly larger diameter (125) that is 50% larger than the native artery diameter and 50% larger than the non-focal region diameter (128) to generate a compressive force onto the sympathetic nerves (70) within the vessel wall. The nerve fibers are blocked by either severance of the nerve fibers or via compression of the nerve fibers. The luminal fabric or luminal covering (155) can be formed from materials such as ePTFE, microporous PU (5-30 micron pore sizes), or other thin microporous materials used in vascular grafts or other implanted medical devices.

Figure 10B:
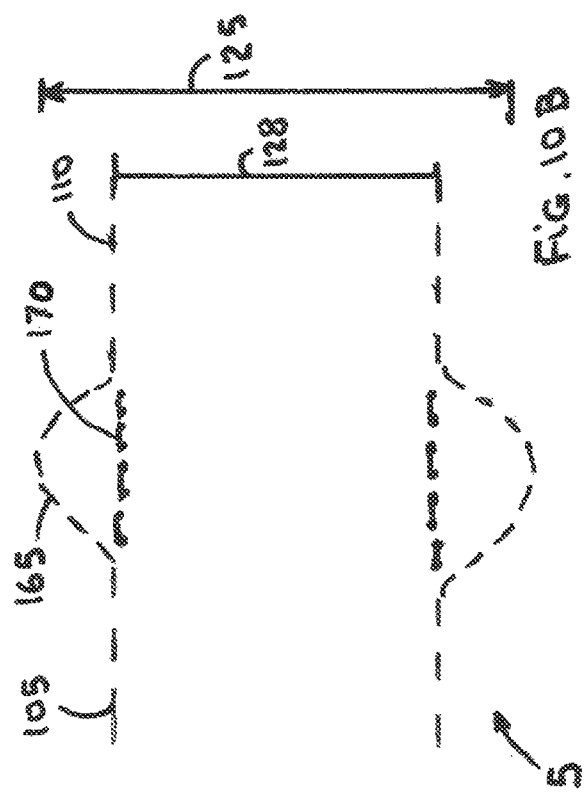
FIG. 10B is a longitudinal view of a compression stent held in an expanded configuration; the compression stent has an outer stent focal region and an luminal stent.
Figure 10A:
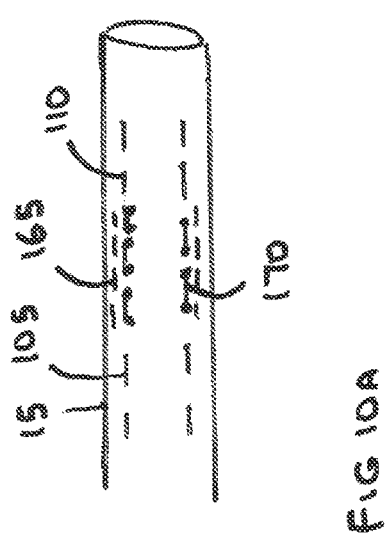
FIG. 10A is a longitudinal view of a compression stent held in a nonexpanded configuration in an external sheath; the compression stent has an outer stent focal region and an luminal stent.

Another embodiment for a SE compression stent (5) is shown in FIGS. 10A and 10B. The proximal region and distal region of the stent are formed from SE material such as NiTi. The compression stent (5) has an outer stent focal region (165) and a luminal stent region (170); both are formed from SE materials in this embodiment. The outer stent focal region (165) is sized to be significantly larger (50% larger, range 30-100% larger) than the native lumen diameter; the luminal stent is sized such that it retains the diameter of the stent non-focal regions (152). The SE stent structure can be formed from Nitinol or other elastomeric metal, for example. Upon release of the SE compression stent (5) from the outer or external sheath (15), the compression stent (5) expands outwards such that the proximal and distal stent regions are approximately equal to the native lumen diameter. The outer focal stent expands outwards to a significantly (i.e., 50% larger, range 30-100%) larger stent focal region (100) diameter than the stent non-focal region diameter (128). The luminal stent region (170) has a luminal stent diameter (175) that is approximately equal to the native lumen diameter (35) and is equal to the stent non-focal region diameter (128). The luminal stent region (170) is attached to the proximal region and distal region of the stent and forms a cylindrical tubular stent for blood flow to pass through the lumen. The luminal region and focal region of the stent can be formed via 3D deposition methods of metal, polymer, or composite materials. Alternately, the luminal stent or focal stent can be attached to the proximal region and distal region via metal brazing, welding, or via machining methods commonly used in the formation of stent frame structures. Further alternately, the outer focal stent region can be formed separately and attached to a cylindrical stent that forms the stent proximal region (105), luminal stent region (170), and stent distal region (110); the attachment can occur via brazing, welding, suturing, use of adhesives, or other metal forming process. The proximal and distal stent regions can be formed such that they are contiguous with the focal stent region; the luminal stent region (170) can also be formed contiguously with the other stent portions.

Figure 11:
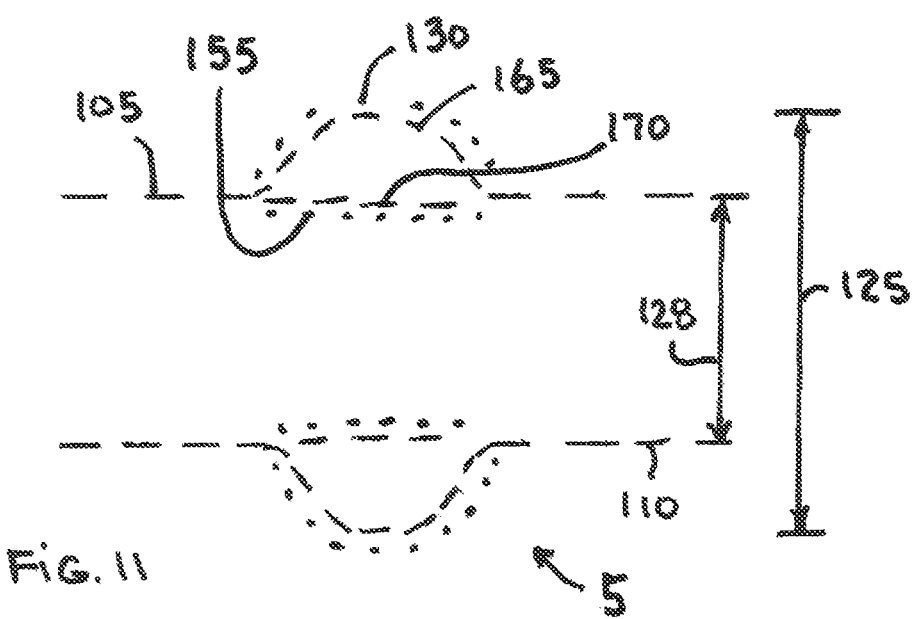
FIG. 11 is a longitudinal sectional view of a compression stent in an expanded configuration with an outer stent focal region, a luminal stent, a focal covering and a luminal covering.

A focal region covering (130) (see FIG. 11) can be bonded or attached to the outer focal stent region or a luminal covering (155) can be attached to the luminal stent region (170) of the compression stent (5) of FIGS. 10A and 10B. The outer focal stent covering (130) will ensure that the focal stent frame does not migrate through the vessel wall but instead applies a pressure to the sympathetic nerve fiber to cause a block in nerve conduction. The luminal stent covering (155) will provide both a cylindrical lumen for blood flow through the renal artery (10) without thrombosis at the site of the enlarged native vessel lumen (30) at the outer stent focal region (165). Also, the luminal covering (155) will prevent migration of SMC into the vessel lumen (30) resulting in stenosis of the artery (10) at the site of the focal region.

The compression stent (5) of the present invention can be formed such that the proximal region and distal region are formed from a BE material and the focal stent region is formed from a SE material as shown in FIG. 12. The BE material is a plastically deformable material such as stainless steel, polymeric materials, biodegradable materials, and other materials commonly used in BE stents including normally elastic metals such as Nitinol or other elastomeric metal which can be machined with hinge geometry that allows the stent non-focal regions (152) of the stent structure to be balloon expandable and undergo plastic deformation during expansion deformation while the stent focal regions can retain the normal elastomeric character of a standard Nitinol stent structure. The BE material can also be formed from a normally elastic material (such as Nitinol, for example) that is thermally treated such that it behaves in a plastically deformable manners. Also, the BE material can be a normally elastic material that is formed into a shape that causes its deformation to occur plastically by exceeding the elastic limit for deformation during its expansion deformation. The BE proximal stent region and BE distal stent region can be formed to be contiguous with the SE stent focal region. With thermal treatment or geometric dimensioning of the stent wall structure the compression stent (5) can obtain balloon expandable character in the stent non-focal regions (152) and self-expanding character in the stent focal regions from a single contiguous metal tube. Alternately, the proximal and distal stent regions can be welded or otherwise attached to the focal stent region. The SE material can be formed from elastically deformable materials such as Nitinol, elgiloy, and other materials commonly used in SE stents.

In its non-expanded configuration as shown in FIG. 12A the compression stent (5) is mounted onto a balloon such as a cylindrical balloon or a dilation balloon (20) with a balloon focal region (135) located at the distal end of a balloon dilation catheter. An external sheath (15) holds the SE focal stent region into a small diameter configuration. Upon release from the external sheath (15) the SE stent focal region (100) can expand out from a smaller nonexpanded diameter to a larger expanded diameter while the BE stent proximal region (105) and stent distal region (110) are crimped tightly to the outside of the dilation balloon. Following expansion of the dilation balloon (20) as shown in FIG. 12B, the SE stent focal region (100) expands outward to its expanded state achieving a stent focal region diameter (125) and causing the vessel wall to compress from larger native wall thickness to a compressed wall thickness; the stent proximal region (105) and stent distal region (110) expand outwards to an expanded state with a larger stent non-focal region diameter (128). Over a time period ranging from minutes to days the stent focal region (100) can expand further to a fully expanded focal region diameter (180) representative of its equilibrium diameter as shown in FIG. 12C. The nerves (70) located within the vessel wall adjacent the focal region are compressed to cause a block in their conduction. The block is due to either a severance of the nerve fiber by the stent frame in the focal region or a compression of the nerve fiber caused by compressive pressure imposed by the focal region. The dilation balloon (20) serves to hold the compression stent (5) in its proper location within the blood vessel while the stent focal region (100) has expanded outwards. The dilation balloon (20) further can serve to provide a post dilation of the stent focal region (100) to effect a more immediate nerve blockage within minutes after implantation. The BE stent proximal region (105) and BE stent distal region (110) are not dilating the native blood vessel significantly (i.e., zero to 15% stent non-focal region diameter (128) oversizing) and hence are nonthrombogenic and are not significantly affecting the vessel native wall thickness.

Figure 13C:
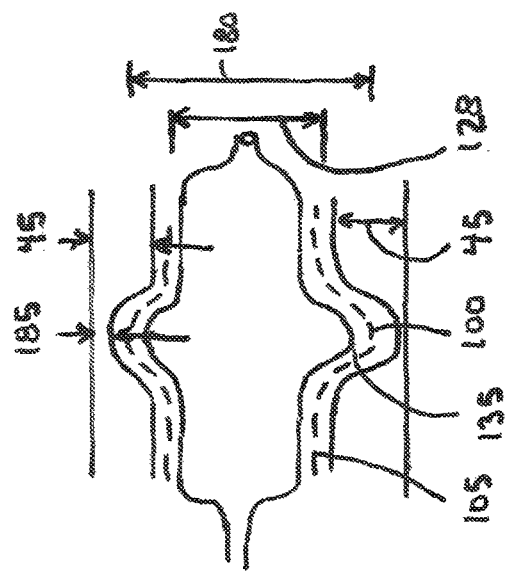
FIG. 13C is a longitudinal view of a compression stent having a self-expanding focal region and balloon expandable non-focal regions; the compression stent has been released from an external sheath and a dilation balloon having a balloon focal region has expanded the balloon-expandable regions and further expanded the self-expanding region causing compression of the blood vessel wall.
Figure 13B:
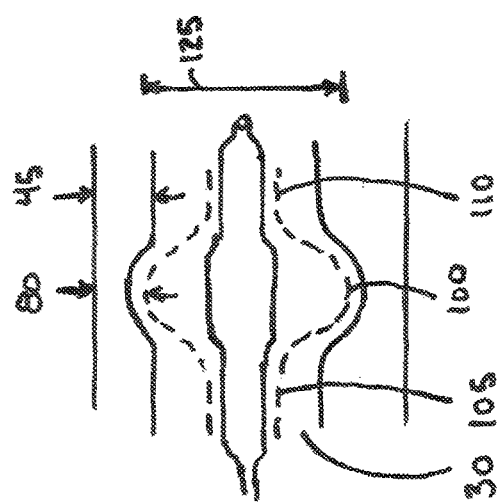
FIG. 13B is a longitudinal view of a compression stent having a self-expanding focal region and balloon expandable non-focal regions; the compression stent has been released from an external sheath but still has the balloon expandable regions mounted onto a dilation balloon; the stent focal region has expanded outwards.
Figure 13A:
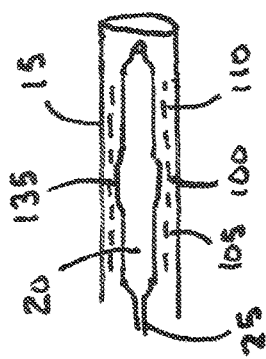
FIG. 13A is a longitudinal view of a compression stent having a self-expanding focal region and balloon expandable non-focal regions; the compression stent is mounted onto a dilation balloon having a balloon focal region and the compression stent is held in an nonexpanded configuration by an external sheath.
Figure 13D:
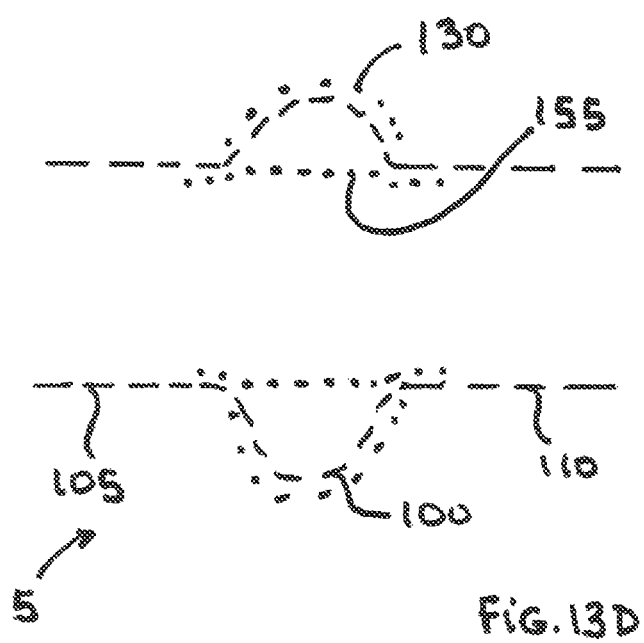
FIG. 13D is a longitudinal view of a compression stent having a self-expanding focal region and balloon expandable non-focal regions; the compression stent has been released from an external sheath and a dilation balloon having a balloon focal region has expanded the balloon-expandable regions and further expanded the self-expanding region; a luminal covering prevents cellular hyperplasia into the lumen.

The compression stent (5) described in the previous embodiment of FIGS. 12A-12C can be mounted onto a dilation balloon (20) that has a balloon focal region (135) as shown in FIGS. 13A-13C. Following release from the external sheath (15) the SE focal stent region (100) will expand outwards to a stent focal region diameter (125) that is significantly larger than the native lumen diameter (35) and the compression stent (5) is held onto the balloon of the balloon dilation catheter (25) via the BE stent proximal region (105) and BE stent distal region (110) of the compression stent (5) as shown in FIG. 13B. Upon expansion of the dilation balloon (20) as shown in FIG. 13C, the focal stent region is pushed outwards into the vessel wall to an even larger fully expanded stent focal region diameter (180) causing even greater compression of the sympathetic nerves (70) found in the vessel wall. The operator is able to identify immediately that the nerve conduction has been blocked. Further expansion of the focal stent region over time may also occur due to remaining expansion forces found in the SE focal region of the stent thereby cause even greater blockage of nerve conduction due to a fully compressed wall thickness (185). The BE stent proximal region (105) and stent distal region (110) are expanded into contact with the vessel wall and have a stent non-focal region diameter (128) that is approximately equal to the native lumen diameter (35) and is significantly smaller than the stent focal region diameter. The compression stent (5) of this embodiment can also contain a focal covering and/or a luminal covering (155) as shown in FIG. 13D. The focal covering can be a thin microporous polymeric material that is attached to the focal region of the stent. The luminal covering (155) can be a thin microporous elastomeric material such as a electrostatically spun PU, a microporous silicone, a composite material or other microporous material that can stretch due to the enlargement of the focal region of the balloon and rebound back to match the native lumen diameter (35) and the stent non-focal region diameter (128). The luminal fabric or luminal covering (155) is attached to both the stent proximal region (105) and stent distal region (110) via adhesive bonding, or cohesive bonds between the polymeric material of the covering (90) and the stent frame material. The luminal fabric or covering can extend into the stent proximal region and into the stent distal region by 3 mm (range 1-10 mm) to ensure that cellular hyperplasic does not result in stenosis of the arterial lumen. The luminal covering can alternately extend throughout the entire non-focal stent regions.

Figure 14C:
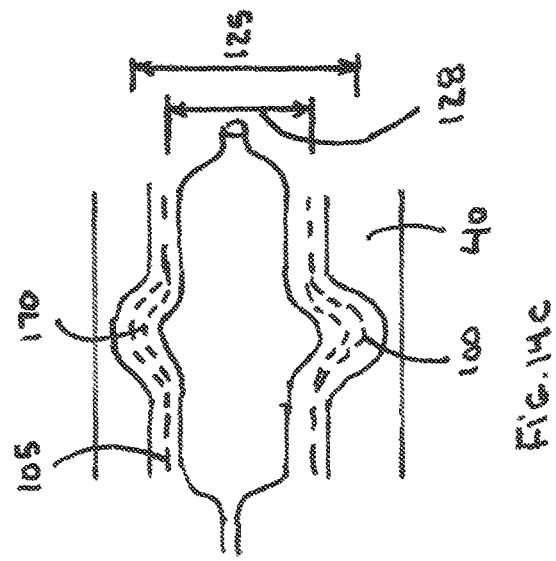
FIG. 14C is a longitudinal view of a compression stent having a self-expanding focal region and balloon expandable non-focal regions; the focal region has a stent focal region and a luminal stent; the compression stent has been released from an external sheath and a dilation balloon having a balloon focal region has expanded the balloon-expandable regions and further expanded the self-expanding region causing compression of the blood vessel wall.
Figure 14B:
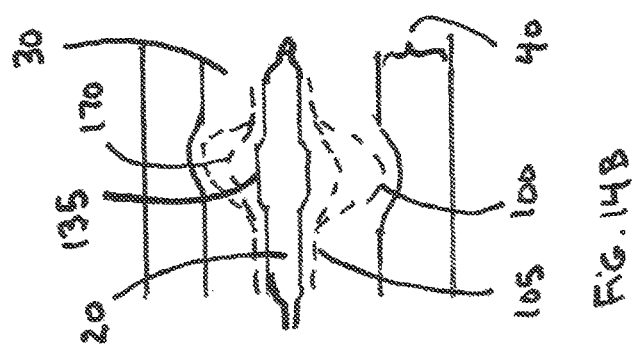
FIG. 14B is a longitudinal view of a compression stent having a self-expanding focal region and balloon expandable non-focal regions; the focal region has a stent focal region and a luminal stent; the compression stent has been released from an external sheath but still has the balloon expandable regions mounted onto a dilation balloon; the stent focal region has expanded outwards.
Figure 14A:
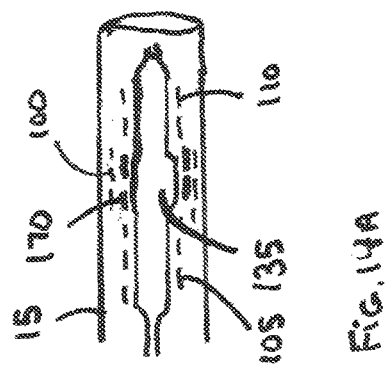
FIG. 14A is a longitudinal view of a compression stent having a self-expanding focal region and balloon expandable non-focal regions; the focal region has a stent focal region and a luminal stent; the compression stent is mounted onto a dilation balloon having a balloon focal region and the compression stent is held in an nonexpanded configuration by an external sheath.

Another embodiment for the compression stent (5) has a BE proximal stent region and BE distal stent region and has a SE focal stent region; a SE luminal stent region (170) is also located adjacent to the focal stent region. The luminal stent can be either welded or bonded to the other regions of the compression stent, or alternately, the luminal stent can be formed contiguously with the other stent regions via 3D machining methods or other machining methods. The compression stent (5) of this embodiment is shown in FIGS. 14A-14C. In FIG. 14A the compression stent (5) is shown loaded onto a balloon having a balloon focal region (135) that is located adjacent the luminal stent region (170). An external sheath (15) holds the SE stent focal region (100) and SE luminal stent region (170) into its smaller diameter configuration. Upon release from the balloon, as shown in FIG. 14B, the SE stent focal region (100) and SE luminal stent region (170) expand outwards to a larger diameter than its smaller delivery configuration diameter. Expansion of the dilation balloon (20), as shown in FIG. 14C causes the BE proximal and BE distal stent regions to expand to a stent non-focal region diameter (128) that is approximately equal (i.e., the non-focal stent region can be zero to 15% larger than the native lumen diameter) to that of the native lumen diameter. The stent focal region (100) and luminal stent region (170) extend outwards to a significantly (i.e., 50% larger, range 30-100% larger) larger stent focal region diameter. Upon deflation and withdrawal of the dilation balloon (20) as shown in FIG. 14D the luminal stent region (170) returns to its luminal stent diameter (175) that is equal to the stent non-focal region diameter (128). The focal stent region will compress the sympathetic nerve fibers and result in nerve block. A focal region covering (130) can be located on the focal stent region and/or a luminal covering (155) can be attached to the luminal stent region (170) as shown in FIG. 14E. The focal covering will cause the focal stent region to apply a pressure to the sympathetic nerve that results in conduction block.

Yet another embodiment for the compression stent (5) has a BE proximal stent region and distal stent region. This embodiment has a BE focal stent region; a SE luminal stent region (170) is located adjacent to the BE focal stent region (100); the stent regions can be formed contiguously or can be joined via various metal joining process methods. The compression stent (5) of this embodiment is shown in FIGS.

15A-15C. In FIG. 15A the compression stent (5) is shown loaded onto a dilation balloon (20) having a balloon focal region (135) that is located adjacent the luminal stent (170). An external sheath (15) may be utilized if necessary to hold the BE focal stent and underlying SE luminal stent region (170) into its smaller diameter configuration. Upon release from the sheath (15), expansion from the balloon, and deflation and removal of the balloon, as shown in FIG. 15B, the BE stent focal region (100) is retained outwards at a larger stent focal region diameter (125) while the SE luminal stent region (170) is returned to its equilibrium luminal stent diameter (175) that is approximately equal to the native vessel diameter and equal to the stent non-focal region diameter (128). The BE proximal and BE distal stent regions have also expanded to the stent non-focal region diameter (128) that is equal to that of the native vessel. The BE focal stent region will compress the sympathetic nerve fibers and result in nerve block via either severance of the nerve fiber or via compression of the nerve fiber. A focal region covering (130) can be located on the stent focal region (100) and/or a luminal fabric or luminal covering (155) can be located on the luminal stent region (170) as shown in FIG. 15C. The focal region covering (130) will cause the focal stent region to apply a pressure to the sympathetic nerve that results in conduction block rather than severing the nerve fiber. The luminal fabric or luminal covering (155) will assist in reducing thrombosis of the native vessel and will prevent migration of SMC into the vessel lumen (30) resulting in vessel stenosis. Alternate embodiments for the compressive stent are contemplated. For example, the luminal stent region (170) of this embodiment can be omitted; alternately the proximal stent region and distal stent region can be formed from a SE material and the focal stent region can be formed from a BE material; such embodiments are anticipated and are included in the present invention.

One or more drugs can be used with any of the embodiments of the present invention to improve their function including reducing thrombosis of the native vessel, reducing restenosis of the native vessel, or improving the ability of the compression device of the present invention to block sympathetic nerve conduction. Drugs can be placed onto the focal region of the stent, the proximal or distal regions of the stent, the luminal stent, the focal covering, or the luminal fabric or luminal covering (155), or any covering (90) located on the stent. Drugs such as Taxol or Sirolimus can be used to reduce cellular SMC proliferation that can lead to vessel stenosis. Anti-thrombotic drugs located on the present invention can reduce thrombosis and enhance patency of the native renal artery (10). Other drugs including such as nerve blocking agents can be applied to any portion of the present invention to assist in causing sympathetic nerve necrosis and reduction of nerve conduction.

The compression stent (5) of the present invention can be formed from a material that allows the stent frame to increase in temperature noninvasively by application of an external energy source including RF, US, focused US, microwave, other electromagnetic energy form, magnetic coupling, IR light, UV light or other energy forms. Energy can be delivered to the compression stent (5) of the present invention via noninvasive coupling and result in sympathetic nerve fiber blockage. The present compression stent (5) is understood to include such designs that contain coils or other coupling means that couple with an external energy sources that are applied noninvasively.

A miniaturized circuit can be located within the stent frame structure (95) of the compression stent (5) that is able to determine if a sympathetic nerve signal is being transmitted across the focal region of the stent or across two focal regions of the compression stent, for example. The miniaturized circuit is initially used during implant of the compression stent (5) to determine if the sympathetic nerve signal is being transmitted across the focal region. If the nerve signal is blocked, then the operator knows that the procedure is completed. If conduction across one or more focal regions of the stent is found then further adjustment of the stent can be performed in the interventional suite. The stent can be examined non-invasively after a period of time to correlate the clinical results with the procedural result. Further dilation of the compression stent (5) can be performed using noninvasive energy coupling to the stent.

Reference numerals used to describe structural elements of one embodiment are intended to be applied to another embodiments to describe the same structural element and have the same description for all similar structural elements. Other embodiments of the present invention are anticipated and the presented embodiments are not intended to limit the scope of the invention.

The invention claimed is:

1. A compression stent assembly for implantation into an artery via catheter delivery in a smaller diameter configuration and expandable to a larger diameter configuration, said compression stent assembly comprising;
    A. a compression stent having a stent focal region positioned between a stent proximal non-focal region and a stent distal non-focal region, said stent focal region being formed from a material that is self-expanding and having elastic character, said stent proximal non-focal region or said stent distal non-focal regions being formed from a material that is balloon expandable and having plastic character, said compression stent being contained within an external sheath during delivery, said external sheath holding said stent focal region into said smaller diameter configuration, said stent focal region having at least a 30% larger stent focal region diameter than a stent non-focal region diameter for said stent proximal and distal non-focal regions in said larger diameter configuration,
    B. said compression stent being mounted onto a dilation balloon positioned at a distal end of a balloon dilation catheter, said dilation balloon having a balloon focal region and a balloon non-focal region, said balloon focal region having a balloon focal region diameter that is larger than a balloon nonfocal region diameter with said dilation balloon in a dilated configuration, said balloon focal region being positioned radially adjacent to said stent focal region,
    C. a focal covering comprising a thin polymeric material attached to said compression stent, said focal covering extending throughout said stent focal region, said focal covering able to prevent cells from the artery from migrating from a region outside of said focal covering into a lumen of said compression stent, said focal covering able to prevent migration of said stent focal region into the a wall of the artery.

2. The compression stent assembly of claim 1 further comprising a luminal covering extending within said stent proximal non-focal region and said stent distal non-focal region, said luminal covering comprising a thin polymeric material having a luminal covering diameter with said compression stent assembly in said larger diameter configuration, said luminal covering diameter being equal to said stent non-focal region diameter.

3. The compression stent assembly of claim 1 further comprising a stent luminal fabric positioned radially adjacent to said focal region, said luminal fabric being formed from a thin cylindrical polymeric material, said luminal fabric having a luminal fabric diameter in with said compression stent assembly in said larger diameter configuration, said luminal fabric diameter being equal to said stent non-focal region diameter.

4. The compression stent assembly of claim 1 wherein said stent focal region diameter is at least 50% larger than said stent non-focal region diameter.

5. The compression stent assembly of claim 1 wherein said stent focal region diameter ranges from 30-100% larger than said stent non-focal region diameter.

6. The compression stent assembly of claim 1 wherein said focal covering attached to said stent focal region is formed from a material that can stretch to an expanded diameter, said expanded diameter being at least 30% larger than said non-focal region diameter.

7. The compression stent assembly of claim 1 wherein said balloon focal region expands to said stent focal region diameter upon expansion of said dilation balloon.

\* \* \* \* \*